United States Patent [19]
Hansen et al.

[11] Patent Number: 5,104,034
[45] Date of Patent: Apr. 14, 1992

[54] PERFLUORO-N,N,N',N-TETRAPROPYL-DIAMINOPROPANE AND USE THEREOF IN VAPOR PHASE HEATING

[75] Inventors: John C. Hansen, Lakeland; George G. I. Moore, Afton, both of Minn.

[73] Assignee: Minnesota Mining and Manufacturing Company, St. Paul, Minn.

[21] Appl. No.: 683,991

[22] Filed: Apr. 11, 1991

Related U.S. Application Data

[62] Division of Ser. No. 423,891, Oct. 19, 1989.

[51] Int. Cl.$^5$ ............................................. B23K 1/015
[52] U.S. Cl. .................................................... 228/242
[58] Field of Search ....................... 228/240, 242, 219

[56] References Cited

U.S. PATENT DOCUMENTS

| Re. 30,399 | 9/1980 | Ammann et al. | |
|---|---|---|---|
| 2,519,983 | 8/1950 | Simons. | |
| 2,616,927 | 11/1952 | Kauck et al. | |
| 2,713,593 | 7/1955 | Brice et al. | |
| 4,238,186 | 12/1980 | Pfahl, Jr. | |
| 4,549,686 | 10/1985 | Sargent et al. | |
| 4,788,339 | 11/1988 | Moore et al. | |
| 4,925,992 | 5/1990 | Schweighardt et al. | 228/240 |

FOREIGN PATENT DOCUMENTS 63-89690 4/1988 Japan.

OTHER PUBLICATIONS

"Condensation Soldering: A New Mass Soldering Process" by R. C. Pfaht, Jr. et al., Welding Journal, Jan. 1975.
"Mass-Soldering Equipment for the Electronic Industry" by S. Karpel, Quarterly Journal of The International Tin Research, No. 130 (1981), pp. 1-3.
"Vapor-Phase Soldering with Perfluorinated Insert Fluids", Proceedings of Technical Program NEPCON 1979, Anaheim, Calif. 1979.
Electronic Production, Jul., 1985, pp. 47, 49.
3M Bulletin No. 98-0211-4411-2 (78.2) RI, XY, issued Jun. 1988.
Chemistry Express, vol. 3, No. 3, pp. 191-194 (1988).
3M's Bulletin, 98-0211-4542-2, issued Mar. 1989.
H. Finch, et al., Jour. Am. Chem. Soc. 74, 2016 (1952).

*Primary Examiner*—Samuel M. Heinrich
*Attorney, Agent, or Firm*—Gary L. Griswold; Walter N. Kirn; Carolyn V. Peters

[57] ABSTRACT

N,N,N',N'-tetrapropyldiaminopropane is fluorinated to produce a liquid predominantly perfluoro-N,N,N',N'-tetrapropyldiaminopropane, having inert properties and a boiling point in the range of 212° C. to 216° C. The inert liquid product is useful as a heat transfer liquid.

4 Claims, No Drawings

PERFLUORO-N,N,N',N-TETRAPROPYL-DIAMINOPROPANE AND USE THEREOF IN VAPOR PHASE HEATING

This is a division of application Ser. No. 07/423,891 filed Oct. 19, 1989.

This invention relates to perfluorinated tertiary amine liquids and their hydrocarbon precursors, to their preparation, and to the use of perfluorinated tertiary amine liquids as heat transfer fluid in vapor phase (or condensation) heating processes, such as reflow soldering of printed circuit boards and other devices.

The development of mass soldering techniques has played an important role in the phenomenal growth of the electronics industry. A significant milestone in the advancement of this technology was the introduction in 1975 of vapor phase (or condensation) heating in soldering operations by the Western Electric Company, Inc. —see for example U.S. Pat. No. 30,399 (Ammann et al) and 4,238,186 (Pfahl); "Condensation Soldering: A New Mass Soldering Process" by T. Y. Chu et al in *Welding Journal*, April, 1975; and "Mass-Soldering Equipment For The Electronic Industry" by S. Karpel in the *Quarterly Journal of The International Tin Research Industry Institute*, No. 130 (1981), pages 1–3.

Briefly, the vapor phase soldering process comprises heating a pool of an inert perfluorinated liquid to boiling in a tank to form a saturated vapor of the liquid in the space between the boiling liquid and a condensing coil, immersing in the vapor the workpiece to be soldered, e.g. a printed circuit board with pre-applied solder, so that the workpiece is enveloped by the vapor, allowing the vapor to condense on the relatively cool surface of the workpiece to thereby enable the vapor to give up its latent heat of vaporization so as to melt and reflow the solder on the workpiece, and then removing the soldered workpiece from the vapor.

The vapor phase soldering process was first commercialized when Minnesota Mining and Manufacturing Company ("3M") provided as heat transfer fluid for this process a product called Fluorinert Electronic Liquid FC-70, a perfluoroalkyl tertiary monoamine liquid boiling at about 215° C. That temperature is ideal for tin-lead solder alloys and the electronic circuit board materials used for most electronic applications. Further, that 215° C. temperature is now a standard operating temperature for vapor phase soldering, and any heat transfer fluid used or proposed for such operation is usually required to have a boiling point of about 215° C.

Said 3M Fluorinert product is made by an electrochemical fluorination process comprising electrolyzing the hydrocarbon analog precursor with anhydrous hydrogen fluoride, a reaction in which carbon-bound hydrogen atoms are replaced with fluorine atoms. A more highly thermally stable product of this type is sold by 3M as Fluorinert TM Electronic Liquid FC 5312. These products and the vapor phase condensation heating technology are described by R. D. Danielson in "Vapor-Phase Soldering with Perfluorinated Inert Fluids," Proceedings of Technical Program NEPCON, 1979, Anaheim, California, 1979, and in 3M's bulletin, "Fluorinert TM Liquids Vapor Phase Heating References," No. 98-0211-43775(58.5) BG, issued May, 1988. ("Fluorinert" and "FC" are trademarks of 3M.)

Because of the formation during vapor phase soldering of trace amounts of perfluoroisobutylene("PFIB") and hydrogen fluoride ("HF") as toxic decomposition products of fluorinated fluids, safety-related and corrosion-related issues have led to the need for heat transfer fluids which produce lower amounts of PFIB and HF. Concern about these toxic compounds is described, for example, in *Electronic Production*, July, 1985, pages 47, 49, and in 3M Bulletin No. 98-0211-4411-2(78.2) R1 XY, issued June, 1988. The aforementioned Fluorinert TM Liquid FC-5312 is more thermally stable than Fluorinert TM Liquid FC-70. And the use of perfluorotetradecahydrophenanthrene as a heat transfer fluid is disclosed in U.S. Pat. No. 4,549,686 (Sargent et al) as not producing detectable amounts of PFIB and HF. The latter fluorinated fluid is one of the few known fluorinated liquids which boil at 212°–216° C., or about 215° C., the industry-set operating temperature standard for vapor phase soldering.

Briefly, in one aspect of this invention, a novel perfluorinated inert liquid comprising predominantly perfluoro-N,N,N',N'-tetrapropyldiaminopropane is provided. The propyl groups can be normal or branched and the same or different and the propylene moiety bonded to the two amino nitrogen atoms can be straight or branched; the preferred diamino compound is perfluoro-N,N,N',N'-tetra-n-propyl-1,3-diaminopropane. The liquid boils at 212° to 216° C., or about 215° C., and, as indicated by its perfluorinated inert character, is essentially free of hydrogen, chlorine, and bromine atoms, and is advantageously chemically inert and stable, thermally stable, non-oxidizing, electrically non-conducting, and non-flammable and boils to produce vapors with the same said properties as the liquid. Those properties, together with the vapor's relatively high density and high latent heat of vaporization, make the liquid particularly useful as a heat transfer (or working) fluid for vapor phase (or condensation) heating operations, such as soldering. When used for such operations, the liquid produces significantly low amounts of PFIB and HF and very little "fog"(and thus low fluid loss). Its use also results in less "wash-off" of commercial solder fluxes (and thus the function of the fluxes is maintained and there is minimum contamination of the liquid with flux). The liquid also has a relatively low pour point, a wide liquid range, and relatively low viscosity, all of which properties facilitate its handling and use over wide temperature ranges.

The perfluorinated inert liquid of this invention (referred to herein as the "perfluoro diamine") can be prepared by electrochemical fluorination. The latter is a known type of a highly energetic reaction which is often accompanied by carbon-carbon bond cleavage that leads to fragmentation and recombination phenomena and results in the formation of low and high molecular weight by-products. Those by-products include tars that often deposit on the electrodes of the electrochemical cell and impede current flow, with corresponding increase in the voltage necessary to continue the electrochemical reaction. That increase in voltage results in increased fragmentation and eventual current stoppage and arrest of the electrical fluorination reaction. These problems become aggravated when the number of carbon atoms in the compound used as the cell feed, i.e., the organic substance being fluorinated, is relatively high, e.g. more than 12 carbon atoms. Surprisingly and notwithstanding the relatively high number of carbon atoms, namely 15, in the hydrocarbon used as precursor cell feed for the perfluoro diamine of this invention, this perfluorinated liquid can be produced by electrochemical fluorination at relative low voltage and with relatively low amounts of by-products, the major condensible by-product in the cell product being perfluorotripropylamine, which can be readily separated, e.g. by simple distillation to yield the perfluoro diamine as a distillate.

The perfluoro diamine of this invention obtained as said distillate comprises predominantly the perfluoro-N,N,N',N'-tetrapropyldiaminopropane compound and a minor amount of perfluorinated compound(s) with essentially the same boiling point as the perfluoro diamine compound Generally, the distillate will contain at least 70 weight percent, and even as high as 95 weight percent, of the perfluoro diamine compound, and the balance will be the other perfluorinated compound(s) which comprise cyclic derivatives of the hydrocarbon cell feed, N,N,N',N'-tetrapropyldiaminopropane, and homologs and isomers of the perfluoro derivative thereof. The distillate will have a boiling point in the range of 212° to 216° C., or about 215° C., the particular boiling point for a particular distillate product depending on the amount of by-products still present therein, the typical boiling point being 214° C. at 740 torr.

The yield of the perfluoro diamine distillate can be, in the case of perfluoro-N,N,N',N'-tetra-n-propyl-1,3-diaminopropane, as high as 40 percent, based on the hydrocarbon diamine precursor used as cell feed, such yield being surprisingly high in view of the yield of only about 5 percent for the perfluoro-N,N,N',N-tetra-n-propyl-1,2-diaminoethane product produced by electrochemical fluorination of its hydrocarbon analog under comparable conditions. Said high yield of the perfluoro diamine is also surprising in view of yields which are merely detectible (by gas-liquid chromatography) of perfluoro-N,N,N',N'-tetra-n-butyl-1,2-diaminoethane (a perfluoro compound disclosed in said U.S. Pat. No. 2,616,917) produced by electrochemical fluorination under comparable conditions from its hydrocarbon precursor. The high yield is further surprising in view of the low yields of perfluoro-N,N,N',N'-tetraethyl-1,3-diaminopropanes (b.p. about 170° C.) made by electrochemical fluorination, as disclosed in Chemistry Express, Vol. 3, No. 3, p. 191–194 (1988).

The perfluoro diamine liquid of this invention can be prepared by electrolyzing a solution of liquid, anhydrous hydrogen fluoride containing the corresponding hydrocarbon liquid precursor, N,N,N',N'-tetrapropyldiaminopropane, the propyl and propylene moieties of which can likewise be straight or branched chain, N,N,N',N'-tetra-n-propyl-1,3-diaminopropane being a preferred. The electrochemical reaction can be carried out in an electrolytic cell employing a nickel anode and an iron or steel cathode, as described, for example, in U.S. Pat. Nos. 2,519,983 (Simons), 2,616,927 (Kauck et al.), and 2,713,593 (Brice et al.). The crude perfluorinated liquid product removed from the cell can be treated to remove residual HF by-product, for example by treating the crude cell product with NaF, then fractionally distilling it in one or more steps and treating with caustic, e.g. as described in U.S. Pat. No. 4,788,339 (Moore et al). A working example is hereinafter set forth of the preparation of the perfluoro liquid of this invention.

The perfluoro diamine of this invention can be used in the vapor phase heating of an article. In such a process, a fluorinated liquid is boiled to produce a saturated vapor which contacts the article to be heated, the vapor condensing on the relatively cool surface of the article and raising its temperature to achieve a desired purpose, e.g. to cure a polymeric or resinous protective coating on the article, e.g. an optical lens, the improvement in such process being the use of the perfluoro diamine.

In using the perfluoro diamine as a heat transfer fluid in vapor phase (or condensation) soldering, the manipulative steps and equipment therefore can be the same as that used with a fluorinated liquid such as Fluorinert ™ Liquid FC-70, e.g. as described in said 3M bulletin No. 98-0211-4377-5(58.5)BE. Such process comprises heating in a tank of a soldering system a pool or body of the perfluoro liquid of this invention to its boiling point, e.g. about 215° C., to form and maintain a body or zone of saturated vapor thereof at the same temperature in a space between the boiling liquid and condensing means such as cooling coils, immersing in said body of vapor a relatively cool workpiece assembly to be soldered, e.g., a printed circuit board with surface-mounted, pre-applied solder, allowing the vapor to condense on the workpiece assembly and give up its latent heat of vaporization so as to raise the solder to the boiling point of the perfluoro diamine liquid and cause melting and reflow of the solder, and then removing from the soldering system the workpiece with its resulting solder joints. The reflow of the solder takes place in the vapor zone of the soldering system since the temperature of the vapor is higher than the melting point of the solder but not so high that it damages the workpiece. The boiling point of the perfluoro diamine is also ideal for the tin/lead solders melting below 214° C. and for circuit board materials used in most electronic applications. All tin/lead compositions with Sn/Pb weight ratios ranging from 55/45 to 80/20 are liquid from 183° C. to 204° C. Typical solders which can be reflowed with the vapors of the perfluoro liquid of this invention are 63Sn/37Pb, 60Sn/40Pb, 62Sn/36Pb/2Ag, and 50Pb/50In. The solder can be pre-applied to the workpiece in the common ways now used in mass reflow soldering operations. Since the vapor phase soldering environment is essentially oxygen-free, a less active flux can be used or, in some cases, no flux at all.

The soldering system used with the perfluoro diamine can be either a batch system or a continuous in-line system. For batch soldering, workpiece assemblies are lowered vertically into the saturated vapor zone. A secondary vapor blanket may be used to help contain the primary vapor in the unit. In-line vapor phase soldering uses a continuous conveyor to transport assemblies horizontally through the saturated vapor zone. Said U.S. Pat. No. 30,399 illustrates equipment which can be used in such batch and continuous systems, and there are a number of liquids commercially available which can be used to provide secondary vapors, such as 3M SF-2 Secondary Fluid described in 3M's bulletin 98-0211-4542-2, issued March of 1989.

In batch soldering units, the reflow time will depend on the surface area and mass of an assembly and must be determined for each application. In most situations, reflow time will range from approximately 15 to 30 seconds. For a heavy workpiece, 60 to 90 seconds may be required. For in-line systems, reflow time is dependent on the mass of the workpiece, but usually will be 10 to 20 seconds for small pieces.

There is a host of electronic assemblies which can be soldered by vapor phase heating and such assemblies can likewise be soldered in the practice of this invention, including wire-wrap pin backplane assemblies, printed circuit boards to which tin/lead or tin electroplate is to be fused, terminal configurations which incorporate tin plating on small components or leaded devices, plug-in packages or through-hole components, assemblies involving odd geometries or dissimilar materials such as gyro stator housing, and various devices, board types, and configurations including lead lists and leaded packages, plastic and ceramic devices, ceramic or organic boards, and single or double-sided assemblies which have planar mounting surfaces.

Vapor phase heating equipment which can be used with the perfluoro diamine is available from several manufacturers, all of which equipment have a heat source, such as an immersion heater or a thermal mass system, to generate the vapor zone. An example of a production system which can be used for vapor phase soldering with the perfluoro diamine is the "Phase-Four" production system supplied by Hybrid Technology Corporation ("HTC") and described in its bulletin (undated) on such production systems.

Though the foregoing description focuses on the use of the perfluoro diamine of this invention in vapor phase soldering operations, such liquid can be used as heat transfer medium in other vapor phase heating applications where a rapid heat transfer is advantageous, such as in the processing of various polymers, epoxies, metals, and coatings, e.g. in the curing of thermosetting resin coatings.

The perfluoro diamine of this invention can be made, as discussed above, by the electrochemical fluorination of its corresponding hydrocarbon liquid precursor, which is preferably N,N,N',N'-tetra-n-propyl-1,3-diaminopropane. That precursor in turn can be made by reacting dipropylamine with acrolein or with either 1,3-dichloropropane or 1,3-dibromopropane, as illustrated in the following reaction schemes:

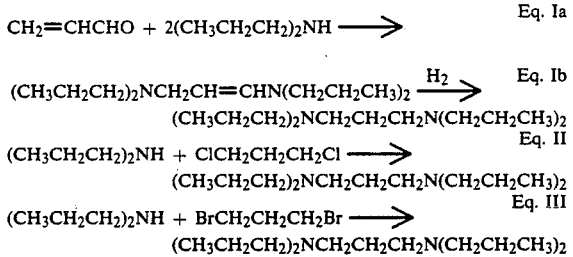

In the reaction of Eq. Ia, acrolein is reacted with two equivalents of dipropylamine to produce the intermediate enamine, which is catalytically hydrogenated or reduced in the reaction of Eq. Ib to the desired precursor N,N,N40 ,N'-tetra-n-propyl diaminopropane. Solvents can be used in each step, such as ethyl acetate, isopropanol, methylene chloride, and excess dipropylamine (but, surprisingly, not methanol and toluene). A dehydrating agent, such as $MgSO_4$, $Na_2SO_4$, or zeolite, may be used to remove by-product water that results from the reaction of Eq. Ia. (These dehydrating agents can be present during the reduction of Eq. Ib). Alternatively, the water resulting from the reaction of Eq. Ia may be removed as a separate phase, if a solvent such as ethyl acetate is used, or it can be left present in carrying out the reaction of Eq. Ib. Acceptable reduction catalysts include platinum, palladium, and Raney nickel, platinum-on-carbon being preferred. The reduction temperature and pressure are relatively mild (25° C. and 0.5 mPa). The success of this reduction is surprising in view of the reported instability of N,N,N',N'-tetra-isopropyl-1,3-diaminopropane (see H. Finch, et al. *Jour.* *Am. Chem. Soc.* 74, 2016 (1952)) and the failure of this material to reduce to the corresponding 1,3-diaminopropane.

The alternative routes illustrated by Eqs. II and III involve nucleophilic displacement of chloride and bromide, respectively, from the corresponding 1,3-dihalopropane by 2 equivalents of dipropylamine. The dichloropropane is preferably reacted in dimethylformamide solution at 130° C., while the dibromopropane reacts readily with neat dipropylamine at 90° -100° C.

An isomeric perfluoro diamine can be prepared by electrochemical fluorination of N,N,N',N'-tetrapropyl-1,2-diaminopropane. This precursor can abe prepared in reactions analogous to Eqs. II and III, starting with the 1,2-dihalopropane. In all of the above reaction schemes, N-isopropyl groups can replace some or all N-n-propyl groups, to lead to perfluoro diamines in which some or most of the perfluoro-N-propyl groups are isopropyl.

Objects and advantages of this invention are illustrated in the following examples.

EXAMPLE 1

A mixture of 41.4 g (0.41) mol dipropylamine, 10 g $MgSO_4$, and 100 mL ethyl acetate was cooled to 10° C. and 14 mL (0.2 mol) acrolein was added dropwise over 30 min. The temperature was maintained at 10°-15° C. The resulting mixture was allowed to warm to room temperature and stirred 3 hr. The $MgSO_4$ was filtered and the ethyl acetate solution was flushed well with $N_2$ before addition of 0.15 g 5% palladium on carbon. The resulting enamine solution was then placed on a Parr low pressure hydrogenator at 0.35 MPa (50 psig $H_2$). After 24 hr, the hydrogenated mixture was filtered and distilled to 27.7 g of N,N,N',N'-tetra-n-propyl-1,3-diaminopropane distillate (representing a yield of 58%), bp 120°-30° C./10 torr, and a residue of 1.7 g. The distillate can be used as feed for electrochemical fluorination to produce the perfluoro diamine of this invention; alternatively, said hydrogenated mixture can be filtered and stripped and used as said feed.

EXAMPLE 2

A mixture of 18.2g (0.16 mol) 1,3-dichloropropane and 100 mL dipropylamine was heated at reflux (94° C.) for 17 hr. Gas-liquid chromatography (glc) of a base-washed aliquot showed 1% of the mixture was the desired diamine product. After addition of 25 mL dimethylformamide, the mixture was heated at 130° C. for 3 hr, forming a white slurry. Glc now showed the product to contain 45% dipropylamine, no dichloride, 7% mono amine, and 44% desired diamine. The mixture was washed with aqueous NaOH and the upper organic layer was distilled to yield 31.6g of the diamine (a 40% yield) boiling at 80°-88° C./0.3 torr. Glc showed the product to be 94% N,N,N',N'-tetra-n-propyl-1,3- diaminopropane, the purity being confirmed by nmr.

EXAMPLE 3

A solution of di-n-propylamine (45 g, 0.45 mol) in 20 mL isopropanol was stirred at reflux (92° C.) while adding 20.2 g (0.1 mol) 1,3-dibromopropane. A very slight exotherm was noted. The mixture formed a mobile slurry of HBr salts in 1 hr. The glc of aliquots of the slurry quenched in dilute NaOH showed the reaction to be complete in 1.5 hr. The mixture on cooling remained an easily stirred slurry. Addition of a solution of 9 g (0.225 mol) NaOH in 20 mL water neutralized the HBr and caused separation of the product and unreacted dipropylamine as a clear, thin, upper layer. Distillation first yielded dipropylamine at 50°/15 torr and then 44.6 g of the N,N,N',N'-tetra-n-propyl-1,3-diaminopropane (a yield of 90%) with a bp of 120°-30° C./15 torr.

EXAMPLE 4

A mixture of 45 g (0.45 mol) dipropylamine, 20 mL isopropanol, 10 g NaOH, and 20 mL H20 was heated to near-reflux and 40.4 g (0.2 mol) 1,3-dibromopropane was added over 5 min. After 3 hrs at reflux, the mixture was cooled and the upper, organic phase was separated and amounted to 39.3 g of essentially pure N,N,N',N'-tetra-n-propyl-1,3-diaminopropane, the yield being 91% of the crude diamine product.

EXAMPLE 5

A 50-ampere electrochemical fluorination cell of the type described in U.S. Pat. No. 2,713,593 was charged with 1500 g liquid anhydrous hydrogen fluoride. N,N,N',N'-tetra-n-propyl-1,3-diaminopropane (833 g), prepared as described in Example 3, was charged periodically to the cell with additional anhydrous hydrogen fluoride as needed. The cell was operated continuously at 5.0 to 6.0 volts, 30 amperes, 40° to 50° C. and 0.20 to 0.28 MPa. The condensable gaseous products were recycled to the cell, and the liquid fluorocarbon product mixture, present as a lower layer, was separated from the hydrogen fluoride layer to yield 2218 g of crude fluorochemical product. Some of the crude perfluorinated product was treated with a small amount of NaF to remove residual hydrogen fluoride and fractionated, initially by heating under a 3-plate Snyder distillation column until the head temperature reached 195° C. and then distilled in a one-plate mode to a heart cut of distillation range 202° 227° C. This product was treated with caustic as described in said U.S. Pat. No. 2,616,927 to produce a stable perfluoro-N,N,N',N'-tetra-n-propyl-1,3-diaminopropane product, the yield being 38%.

Another portion of the crude perfluorinated product was treated with caustic and fractionated on a one meter distillation column, packed with glass helices, to give a heart cut of distillation range of 200°-214° C. The fractionated material was treated with excess potassium permanganate in acetone and washed well with acetone, to provide perfluoro-N,N,N',N'-tetra-n-propyl-1,3diaminopropane product free of oxidizable trace impurities. Analysis by H-nmr showed the caustic-treated material to contain very little hydrogen, namely only 0.026 mg/g. The F-nmr indicated that 92% of the end groups of the product were $-CF_2CF_2CF_3$; the remaining groups were $-CF_3$ (2%) and possibly $-CF_2CF_3$ (6%). Gas chromatography and mass spectral analyses confirmed these assignments, with 95.5% of the end groups identified as $-CF_2CF_2CF_3$. Evidence for the low level presence of cyclic materials was seen by both techniques. This purified perfluoro diamine was characterized for thermal stability, pour point, loss rate, and flux wash-off by the following procedures.

The thermal stability of the perfluoro diamine was determined by heating in the presence of aqueous sodium acetate and subsequently analyzing for fluoride. Thus, a stainless steel tube was charged with 10 g 0.1 molar sodium acetate solution and 10 g fractionated product and then heated at 215° C. for 16 hr. Subsequent analysis for fluoride ion with a fluoride-specific electrode showed 7.2 parts hydrogen fluoride generated per million parts of perfluoro-N,N,N',N'-tetrapropyl-1,3-diaminopropane. In comparison, Fluorinert Liquid FC-70 produced 28 parts hydrogen fluoride per million parts of the Fluorinert Liquid.

Thermal generation of perfluoroisobutylene was also measured by heating the perfluoro diamine at reflux in a three-necked glass flask with a 35 ml/min flow of nitrogen across the liquid and measuring the evolved perfluoroisobutylene with a gas chromatograph calibrated using known dilutions of perfluoroisobutylene in nitrogen. Under standardized conditions, perfluoro-N,N,N',N'-tetrapropyl-1,3-diaminopropane produced 0.032 part perfluoroisobutylene per million parts of refluxing liquid at 2 hrs. In comparison, at 215° C., Fluorinert Liquid FC-70 produced 3.2 parts perfluoroisobutylene.

The pour point of the perfluoro diamine product was found to be $-44°$ C., compared with $-25°$ C. for Fluorinert Liquid FC-70. The kinematic viscosity was 5.8 cs, compared with 14.5 cs for Fluorinert Liquid FC-70.

Loss rate was found by boiling the perfluoro diamine product in a glass resin flask with one L/min air sweep above the boiling liquid, the loss over 24 hr. being 5.2 g/hr. which was the same as that exhibited by Fluorinert Liquid FC-70.

Flux wash-off, a measure of flux solubility, was determined by coating glass slides with "Alpha" 611 flux and immersing these in the vapor zone of a battery jar in which the perfluoro diamine was boiling. The slides were tilted at a slight angle to promote wash-off. After 2 minutes, the slides were removed and the weight loss was recorded. The perfluoro diamine caused a 64% wash-off of flux, whereas by comparison Fluorinert Liquid FC-70 caused 63% wash-off and perfluorotetradecahydrophenanthrene caused 80% wash-off. The latter two observations are consistent with relative flux removal by these liquids in actual use.

Perfluoro diamine of this invention, prepared by electrochemical fluorination in a manner similar to the procedure described above, was effectively used in vapor phase soldering carried out in a HTC 912 vapor phase soldering unit charged with about 3 liters of the perfluoro diamine, heated to a steady state boil, with a vapor temperature of 213° C. at 740 torr. Reflow of 63Sn/37Pb solder on preassembled surface-mounted circuit boards was accomplished in 10 seconds.

Various modifications and alterations of this invention will become apparent to those skilled in the art without departing from the scope and spirit of this invention.

What is claimed is:

1. In a method of vapor phase soldering wherein a component to be soldered is immersed in or enveloped by a body of perfluorinated liquid vapor to melt the solder, and the component is then withdrawn from the body of vapor, the improvement comprising using as the perfluorinated liquid a liquid comprising predominantly perfluor-N,N',N'-tetrapropyldiaminopropane and having a boiling point of about 215° C.

2. In a vapor phase soldering process, comprising heating a pool of inert perfluorinated liquid to boiling in a tank to form a saturated vapor in the space between the boiling liquid and condensing means, immersing in the vapor a workpiece to be soldered whereby the vapor is condensed on the surface of the workpiece so as to melt and reflow the solder, and soldered workpiece is then removed from the space containing the vapor, the improvement comprising using as said perfluorinated liquid a liquid comprising predominantly perfluoro-N,N,N',N'-tetrapropyldiaminopropane and having a boiling point of about 215° C.

3. The method of claim 2, wherein said workpiece carries a solder having a melting point below 214° C.

4. The method according to claim 3, wherein the solder used is a tin/lead solder.

* * * * *

UNITED STATES PATENT AND TRADEMARK OFFICE
CERTIFICATE OF CORRECTION

PATENT NO. : 5,104,034

DATED : April 14, 1992

INVENTOR(S) : Hansen et al.

It is certified that error appears in the above-identified patent and that said Letters Patent is hereby corrected as shown below:

Col. 3, line 11, After "compound" insert --. --

Col. 4, line 50, Replace "usein" with --used in--

Col. 5, line 51, Replace "N,N,N40" with --N,N,N'--

Col. 6, line 13, Replace "abe" with --be--

Col. 7, line 33, Between 202° and 227° insert -- - --

Col. 8, line 51, Replace "perfluor-N,N',N'-tetrapropyldiaminopropane" with --perfluoro-N,N',N'-tetrapropyldiaminopropane--

Col. 8, line 59, Between "and soldered" insert --the--

Signed and Sealed this

Twenty-ninth Day of June, 1993

Attest:

MICHAEL K. KIRK

*Attesting Officer*   *Acting Commissioner of Patents and Trademarks*